(12) United States Patent
Mueller et al.

(10) Patent No.: US 7,141,302 B2
(45) Date of Patent: Nov. 28, 2006

(54) SUTURE MATERIAL FOR SURGERY, PROCESSES FOR ITS PRODUCTION AND THE USE THEREOF

(75) Inventors: Erhard Mueller, Stuttgart (DE); Heinrich Planck, Nuertingen (DE); Sven Oberhoffner, Weinstadt (DE)

(73) Assignee: Deutsche Institute fur Textil-und Faserforschung Stuttgart Stiftung . . ., Denkendorf (DE)

( * ) Notice: Subject to any disclaimer, the term of this patent is extended or adjusted under 35 U.S.C. 154(b) by 249 days.

(21) Appl. No.: 10/014,796

(22) Filed: Dec. 14, 2001

(65) Prior Publication Data

US 2002/0086945 A1    Jul. 4, 2002

(51) Int. Cl.
  *D02G 3/00*    (2006.01)
  *A61B 17/04*   (2006.01)
  *C08G 63/08*   (2006.01)

(52) U.S. Cl. ............... 428/378; 428/375; 428/394; 606/228; 606/230; 528/359; 528/354; 525/413; 525/419

(58) Field of Classification Search ............... 428/375, 428/378, 394, 395; 606/228, 230; 427/2.1, 427/2.31; 525/205, 408, 411, 419, 420, 413; 528/354, 359, 355
See application file for complete search history.

(56) References Cited

U.S. PATENT DOCUMENTS

| | | | |
|---|---|---|---|
| 4,705,820 A | 11/1987 | Wang et al. ................. 524/381 |
| 4,857,602 A * | 8/1989 | Casey et al. ................. 525/408 |
| 4,994,074 A * | 2/1991 | Bezwada et al. ............ 606/230 |
| 5,076,807 A | 12/1991 | Bezwada et al. ............ 606/230 |
| 5,312,642 A * | 5/1994 | Chesterfield et al. ....... 427/2.31 |
| 5,371,176 A * | 12/1994 | Bezwada et al. ............ 528/354 |
| 5,431,679 A | 7/1995 | Bennett et al. .............. 606/230 |
| 5,468,253 A | 11/1995 | Bezwada et al. |
| 5,854,383 A | 12/1998 | Erneta et al. |
| 5,889,075 A | 3/1999 | Roby et al. ................... 522/87 |
| 6,011,121 A | 1/2000 | Goldmann et al. ......... 525/414 |
| 6,031,018 A | 2/2000 | Scopelianos et al. |
| 6,031,069 A | 2/2000 | Oberhoffner et al. |
| 6,165,202 A * | 12/2000 | Kokish et al. ............... 606/230 |
| 6,183,499 B1 | 2/2001 | Fischer et al. |
| 6,235,869 B1 * | 5/2001 | Roby et al. .................. 528/354 |
| 2002/0086945 A1 * | 7/2002 | Mueller et al. .............. 525/205 |

FOREIGN PATENT DOCUMENTS

| | | |
|---|---|---|
| DE | 39 37 272 A1 | 5/1991 |
| DE | 40 03 233 A1 | 8/1991 |
| DE | 196 41 335 A1 | 4/1998 |
| DE | 198 28 416 A1 | 6/1999 |
| EP | 0 608 139 A1 | 7/1994 |
| EP | 0 635 531 A2 | 1/1995 |
| EP | 0 774 265 A1 | 5/1997 |
| EP | 0 839 542 A2 | 5/1998 |
| EP | 0 908 482 A1 | 4/1999 |
| WO | WO 00/01307 | 1/2000 |
| WO | WO 00/16699 | 3/2000 |
| WO | WO 00/22991 | 4/2000 |

* cited by examiner

*Primary Examiner*—Jill Gray
(74) *Attorney, Agent, or Firm*—Nath & Associates PLLC; Gary M. Nath; Tanya E. Harkins

(57) ABSTRACT

A suture material for surgery comprises one or more filaments and is formed with a coating, which is characterized in that the coating at least partly comprises a bioresorbable polymer, which is essentially formed from a random terpolymer with a completely amorphous structure.

8 Claims, No Drawings

SUTURE MATERIAL FOR SURGERY, PROCESSES FOR ITS PRODUCTION AND THE USE THEREOF

DESCRIPTION

The invention relates to suture material for surgery, processes for its production and the use thereof.

In the surgical treatment of injuries or illnesses in human or veterinary medicine the easy handling of suture threads is of considerable importance for a precise suture insertion, together with the durability thereof and complication-free healing after surgery.

Various surgical suture threads of natural and synthetic materials have been developed, which are modified for improving their use characteristics. Thus, it is e.g. known to coat multifilament suture material with fatty acid salts.

However, known coatings suffer from deficiencies with regards to the passing through and knotting behavior. Metal salt coatings tend towards an undesired fluff or dust formation during use. Such coating materials also differ in their physiological behavior, such as in the biodegradability thereof, compared with the suture materials to which they are applied. In addition, the processes for the production of coated suture threads are very complicated and costly.

Therefore the problem of the invention is to make available a suture material, which overcomes the known disadvantages of the prior art materials, which is easy and inexpensive to produce using conventional equipment and which can be used with advantage in surgery.

This problem is solved by a suture material for surgery comprising one or more filaments and formed with a coating, which is characterized in that the coating at least partly comprises a bioresorbable polymer, which is essentially formed from a random terpolymer with a completely amorphous structure. In a preferred embodiment of the invention the bioresorbable polymer can be characterized by waxy properties.

The raw or crude suture material used for coating according to the invention can be constructed in known manner from natural or synthetic filaments in ways known to the expert. For example, it is possible to form monofilaments, multifilaments or combinations of monofilaments and multifilaments of different chemical types to provide suture material. Suitable synthetic filaments are biocompatible, resorbable or non-resorbable polymers such as homopolymers, copolymers, terpolymers or combinations thereof. Examples are polymers based on biocompatible monomers such as glycolic acid, glycolides, lactides, dioxanones, lactones and the like.

With particular advantage with respect to the suture material the terpolymer can be formed using glycolide, ε-caprolactone and trimethylene carbonate and in particular comprises the same. In place of a dimeric glycolide, it is possible to use glycolic acid, so that it is possible to regulate the molecular weight. In the terpolymer glycolide is preferably present in a proportion of 5 to 50 wt. %, ε-caprolactone in a proportion of 5 to 95 wt. %, especially 5 to 90 wt %, and trimethylene carbonate in a proportion of 5 to 95 wt. %, especially 5 to 90 wt %. The weight proportions of the components trimethylene carbonate, ε-caprolactone and glycolide are chosen in such a way that together they represent 100 wt. % of the terpolymer. The terpolymer can also contain trimethylene carbonate and ε-caprolactone in a weight ratio between 95:5 and 5:95, particularly in a weight ratio of 30:70 to 70:30 and preferably 50:50.

It has surprisingly been found that a high molecular weight polymer is suitable as a coating material for surgical suture threads for improving the suture material characteristics and in particular the knotting characteristics. Favourably influenced characteristics are e.g. the knot run, knot seating, knot durability and knot safety.

A higher caprolactone proportion of 5 to 95 wt. % in the terpolymer has a favourable influence on the knot run of the surgical suture material coated therewith. In a preferred embodiment glycolide, caprolactone and trimethylene carbonate can be present in the coating material terpolymer in a percentage weight ratio of 10–20/40–45/40–45.

Advantageously the terpolymer is produced by random copolymerization of glycolide, ε-caprolactone and trimethylene carbonate. The terpolymer can have an average molecular weight in the range of more than 30,000 Dalton. The terpolymer can have a glass transition point in the range −40 to +20° C. and preferably −30 to 0° C. As a result of the amorphous structure and low glass transition point of the terpolymer, the coating composition according to the invention is plastic at room temperature. Another advantage of a suture material coated in accordance with the Invention with a terpolymer having a low glass transition point is its limited flexural rigidity and high flexibility.

To the advantage of the characteristics of the suture material according to the invention, the coating material, particularly the polymer, can have an inherent viscosity of 0.4 to 3.0 dl/g, particularly 0.7 to 1.3 dl/g, measured in HFIP at 25° C. and a concentration of 0.5 wt. %.

The coating material can also contain at least one monofunctional and/or polyfunctional alcohol. In particular, the coating material can contain monofunctional and/or polyfunctional alcohol in a proportion of 0.02 to 8 wt. %. The coating material can also contain at least one monofunctional and/or polyfunctional carboxylic acid, its anhydrides and/or esters. In particular, the coating material can contain monofunctional and/or polyfunctional carboxylic acid and/or derivatives thereof in a proportion of 0.02 to 8 wt. %. In the production of the terpolymer, through the addition of molecular weight regulators such as the aforementioned alcohol and/or carboxylic acid, together with their derivatives, it is possible to reduce the molecular weight of the polymer, so as to obtain an adequately plastic polymer, particularly a waxy polymer. Through an appropriate choice of the nature and quantity of the molecular weight regulator, the molecular weight can be adjusted in a desired manner.

Moreover, by mixing a plasticizer or softener into the terpolymer according to the invention, the plasticity can be further increased. Preference is given to plasticizers which form a compatible mixture with the terpolymer without phase separation occurring. Examples of plasticizers usable according to the invention are fats and oils (e.g. castor oil), the esters and metal salts thereof, glycerin, diethyl phthalates, polyethylene glycol, polypropylene glycol, citrates and phosphates.

The admixing or blending of a plasticizer can take place to the still hot polymer melt directly following on to the polymerization reaction or in a separate process stage. Account must be taken of the thermal stability of the plasticizer. In a preferre embodiment the coating agent can contain at least one plasticizer in a proportion of 1 to 30 wt. %.

Preference is given according to the invention with respect to the suture material to the coating being formed from a combination of bioresorbable polymers with fatty acid salts, particularly calcium stearate and/or magnesium stearate.

The coating material can represent a very high proportion of surgical suture threads. In the suture material according to the invention, the coating agent or material can represent 0.2 to 50 wt. % of the total weight of the coated suture material.

A suture material formed in accordance with the invention is advantageously characterized by a good knot holding capacity and improved knot run behavior compared with known suture materials.

The present invention also relates to a coating material for surgical suture material essentially formed from a bioresorbable polymer and in particular essentially formed from the terpolymer as described hereinbefore. In a preferred embodiment the coating material can be substantially formed from a waxy, bioresorbable polymer.

Advantageously, with respect to the coating material, the terpolymer can be applied to the suture material in the fluid state without solvent, particularly in the melted state.

In a preferred embodiment the coating material can be formed from a combination of the bioresorbable polymer with fatty acid salts, particularly calcium stearate and/or magnesium stearate.

The decomposition of the surgical suture material coating according to the invention takes place in the body of an animal or human by hydrolysis and the body and tissue fluids participate in the latter. As a result of the hydrolysis the polymer chain is cleaved into smaller and more readily soluble fragments. If appropriate, the fragments are further decomposed accompanied by the participation of macrophages. The decomposition products are transported away by the metabolic system and are discharged from the organism as metabolic scums or as carbon dioxide and water. For a good compatibility of the coated suture material in the patient, it is important that during the decomposition process there is no formation or concentration of harmful metabolites. Polyglycolic acid is in particular characterized in that during its decomposition in vivo no toxic degradation products are formed. The trimethylene carbonate and caprolactone used as comonomers according to the invention are also characterized by good compatibility and the avoidance of toxic reactions. The degradation behavior of the terpolymer according to the invention can be modified by varying the total gycolide proportion in the polymer, because in comparison with polytrimethylene carbonate and poly-$\epsilon$-caprolactone, polygycolic acid has a much shorter degradation time.

The invention also relates to a process for the production of a suture material for surgery comprising one or more filaments with a coating and which is characterized in that the coating takes place by the application of a bioresorbable polymer, which is essentially formed from a random terpolymer with a completely amorphous structure. In a preferred embodiment of the invention a waxy, bioresorbable polymer can be applied.

In the process according to the invention, for coating the suture material it is possible to apply a solution of the terpolymer in which said terpolymer is used dissolved in an organic solvent selected from the group of non-toxic, organic solvents, esters, ketones or mixtures thereof. Examples of such solvents are esters such as ethyl acetates and other acetic esters, ketones such as acetone or solvent mixtures. For a coating solution, the terpolymer is preferably dissolved in a concentration of 0.1 to 10, particularly 0.5 to 5 wt. %. Coating solutions prepared for application are advantageously characterized by their stability, even in high concentrations.

In a special embodiment of the process, the surgical suture material for coating can be passed through a solution of the terpolymer. Advantageously the thread is drawn under a slight tension through the coating bath. In general, the coated thread can be supplied to a drying stage directly after extraction from the solution and without any intermediate treatment, such as e.g. stripping.

In a preferred embodiment for coating on the suture material a solution of the terpolymer can be applied by means of a softening stick.

In addition, coating can take place by one or more applicator rolls or in other ways known to the experts.

With particular preference coating can take place at a temperature up to 40° C. and in particular at room temperature. Advantageously, in the process according to the invention, following application of the coating the suture material can be dried using a heating device at 80 to 160° C., particularly 130° C. The suture material is preferably passed in contact-free manner through the heating device. In general, the suture material is not heated to the drying temperature in order to avoid damage to the polymer. It is in particular possible to carry out drying by blowing on heated gas, e.g. warm air. To remove solvent residues, a further drying stage can be performed at reduced pressure, in the range of a few millibars.

When coating using a solution of the polymer, the solvent is evaporated from the coating during the drying process, so that following the removal thereof the coating remains on the suture material in the dry state. Thus, with limited technical effort, in a short time and at low cost a very uniform coating is obtained.

In a special embodiment of the process according to the invention, the coating with terpolymer can take place in the fluid, particularly melted state.

In a further development, the inventive process can be characterized in that the coating takes place with a bioresorbable polymer combined with fatty acid salts, particularly calcium stearate and/or magnesium stearate.

The present invention also relates to the use of a bioresorbable polymer, which is preferably formed essentially from a random terpolymer with a completely amorphous structure as a coating agent or material, particularly on suture material for surgery. A preferred embodiment of the invention can be characterized by the use of a waxy bioresorbable polymer as the coating material.

Further features and details of the invention can be gathered from the following description of preferred embodiments in the form of examples. The individual features can be implemented alone or in subcombinations. The examples merely illustrate the invention and in no way restrict the same.

EXAMPLE 1

250 g of a random terpolymer with the composition glycolide/trimethylene carbonate/$\epsilon$-caprolactone 10/45/45 wt. % are dissolved, accompanied by stirring, in 9750 g of ethyl acetate. The solution is fed into a storage vessel and recirculated by pumping through a smaller container maintained at 22° C. A braided surgical suture thread of thickness USP 2/0 of polyglycolic acid is passed through the solution in the small container and coated with said solution. Immediately thereafter the thread is passed through a heating duct kept at 140° C. and the solvent evaporates. The solvent residue is dried with dry air at approximately 50° C. Approximately 2 wt. % solid constituents remain on the smooth, homogeneously coated suture material.

The suture thread has excellent knot run characteristics, both in the dry and in the wet state. A coated suture thread of thickness USP 1 has comparable characteristics.

EXAMPLE 2

350 g of a random terpolymer of composition glycolide/trimethylene carbonate/ε-caprolactone 10/60/30 wt. % are dissolved, accompanied by stirring, in 9650 g of ethyl acetate. The solution is fed into a storage vessel and recirculated by pumping into a smaller container kept at 22° C. A braided surgical suture thread of thickness USP 3/0 of polyglycolic acid is passed through the solution in the small container and coated with said solution. Immediately thereafter the thread is passed through a heating duct maintained at 160° C. and the solvent is evaporated. The solvent residue is dried with dry air at approximately 50° C. Approximately 3 wt. % solid constituents remain on the smooth, homogeneously coated thread.

The suture material has excellent knot run characteristics, both in the dry and wet state. A coated suture thread of thickness USP 1 has comparable characteristics.

EXAMPLE 3

300 g of a random terpolymer having the composition glycolide/trimethylene carbonate/ε-caprolactone 20/40/40 wt. % are dissolved, accompanied by stirring, in 9700 g of acetone. The solution is fed into a storage vessel and recirculated by pumping into a smaller container kept at 25° C. A braided thread of thickness USP 2/0 of polyglycolic acid is passed through the solution in the small container and coated with said solution. Immediately thereafter the thread is passed through a heating duct, maintained at 160° C. and the solvent evaporates. The solvent residue is dried with dry air at approximately 50° C. Approximately 3 wt. % solid constituents remain on the smooth, homogeneously coated thread.

The suture thread has excellent knot run characteristics, both in the dry and wet state. A coated suture thread of thickness USP 1 has comparable characteristics.

The invention claimed is:

1. A suture material for surgery comprising one or more filaments having a coating thereon, wherein the coating comprises a bioresorbable polymer, which is formed from a random terpolymer with a completely amorphous structure consisting essentially of glycolide, ε-caprolactone and trimethylene carbonate, and wherein the terpolymer contains glycolide in a proportion of 10 to 20 wt. %, with the remainder being ε-caprolactone and trimethylene carbonate in a weight ratio between 30:70 and 70:30, and wherein the terpolymer has a glass transition temperature in the range of −40 to 0° C.

2. Suture material according to claim 1, wherein the terpolymer is produced by random copolymerization of glycolide, ε-caprolactone and trimethylene carbonate.

3. Suture material according to claim 1, wherein the terpolymer has an average molecular weight of more than 30,000 Daltons.

4. Suture material according to claim 1, wherein the coating material further comprises at least one plasticizer in a proportion of 1 to 30 wt. %.

5. Suture material according to claim 1, wherein the coating is formed from a mixture of the bioresorbable polymer with fatty acid salts.

6. Suture material according to claim 1, wherein the coating represents 0.2 to 50 wt. % of the total weight of the suture material.

7. A suture material for surgery comprising one or more filaments having a coating thereon, the coating comprising 0.2 to 50 wt. % of the total weight of the suture material,
  wherein the coating comprises a bioresorbable polymer which is formed from a random terpolymer with a completely amorphous structure consisting essentially of:
  glycolide, ε-caprolactone and trimethylene carbonate;
  wherein the terpolymer contains glycolide in a portion of 10 to 20 wt. %, with the remainder being ε-caprolactone and trimethylene carbonate in a weight ratio between 30:70 m and 70:30; and
  wherein the terpolymer has a glass transition temperature in the range of −40 to 0° C.;
  wherein the coating composition is plastic at room temperature; and
  wherein the suture material has improved knotting characteristics.

8. A suture material for surgery comprising one or more filaments having a coating thereon;
  wherein the coating at least partially comprises a waxy bioresorbable polymer, which is essentially formed from a random terpolymer with a completely amorphous structure;
  wherein the terpolymer consists essentially of a glycolide, ε-caprolactone, and trimethylene carbonate, and the terpolymer contains glycolide in a portion of 10 to 20 wt. %, with the remainder being ε-caprolactone, and trimethylene carbonate in a weight ratio between 30:70 and 70:30;
  wherein the terpolymer has a low glass transition temperature in the range of −40 to 0° C., and a completely amorphous structure;
  wherein the coating material has an inherent viscosity of 0.7 to 1.3 dL/g, as measured in HFIP at 25° C. and a concentration of 0.5 wt. %; and
  wherein the terpolymer is soluble in organic solvents based on esters and ketones or mixtures thereof, the coating composition is plastic at room temperature, the coating represents 0.2 to 50 wt. % of the total weight of the suture material, and the suture material has improved knotting characteristics.

* * * * *

UNITED STATES PATENT AND TRADEMARK OFFICE
CERTIFICATE OF CORRECTION

PATENT NO. : 7,141,302 B2  Page 1 of 1
APPLICATION NO. : 10/014796
DATED : November 28, 2006
INVENTOR(S) : Mueller et al.

It is certified that error appears in the above-identified patent and that said Letters Patent is hereby corrected as shown below:

Title Page, (73) Assignee,

Please delete

"Deutsche Institute fur Textil-und Faserforschung Stuttgart Stiftung..."

and replace with

-- Deutsche Institute fuer Textil-und Faserforschung Stuttgart Stiftung des oeffentlichen Rechts --

Signed and Sealed this

Eleventh Day of November, 2008

JON W. DUDAS
*Director of the United States Patent and Trademark Office*